United States Patent
Lanzano et al.

(10) Patent No.: US 9,110,282 B2
(45) Date of Patent: Aug. 18, 2015

(54) NANOMETER-SCALE OPTICAL IMAGING BY THE MODULATION TRACKING (MT) METHOD

(75) Inventors: Luca Lanzano, Irvine, CA (US);
Michelle Digman, Irvine, CA (US);
Enrico Gratton, San Clemente, CA (US)

(73) Assignee: The Regents of the University of California, Oakland, CA (US)

( * ) Notice: Subject to any disclaimer, the term of this patent is extended or adjusted under 35 U.S.C. 154(b) by 457 days.

(21) Appl. No.: 13/435,387

(22) Filed: Mar. 30, 2012

(65) Prior Publication Data

US 2012/0250000 A1 Oct. 4, 2012

Related U.S. Application Data

(60) Provisional application No. 61/469,715, filed on Mar. 30, 2011.

(51) Int. Cl.
| | |
|---|---|
| *G01C 3/08* | (2006.01) |
| *G02B 21/00* | (2006.01) |
| *G01B 9/04* | (2006.01) |
| *G01N 21/64* | (2006.01) |
| *B82Y 35/00* | (2011.01) |

(52) U.S. Cl.
CPC ............. *G02B 21/0012* (2013.01); *G01B 9/04* (2013.01); *G01N 21/6458* (2013.01); *B82Y 35/00* (2013.01); *G02B 2207/113* (2013.01)

(58) Field of Classification Search
CPC ......... G01S 17/36; G01S 17/89; G01S 7/497; G01S 17/32; G01C 3/08
USPC .................... 356/3.01, 5.1, 5.01, 4.01, 9, 625
See application file for complete search history.

(56) References Cited

U.S. PATENT DOCUMENTS

| | | | | |
|---|---|---|---|---|
| 6,052,478 | A * | 4/2000 | Wihl et al. ..................... | 382/144 |
| 7,248,342 | B1 * | 7/2007 | Degnan ......................... | 356/5.01 |
| 7,358,890 | B2 * | 4/2008 | Price et al. ...................... | 342/82 |
| 7,476,787 | B2 * | 1/2009 | Thomas et al. ................ | 250/306 |
| 7,902,523 | B2 * | 3/2011 | Motomura ................... | 250/458.1 |
| 8,319,951 | B1 * | 11/2012 | Troy ............................. | 356/5.01 |
| 8,557,576 | B2 * | 10/2013 | Clarke et al. .................. | 435/347 |
| 2004/0036884 | A1 * | 2/2004 | Unlu et al. .................... | 356/455 |
| 2010/0303344 | A1 * | 12/2010 | Sato et al. ..................... | 382/162 |
| 2013/0212537 | A1 * | 8/2013 | Hall .............................. | 715/849 |

* cited by examiner

*Primary Examiner* — Isam Alsomiri
*Assistant Examiner* — Samantha K Abraham
(74) *Attorney, Agent, or Firm* — Marcus C. Dawes; Daniel L. Dawes (57) ABSTRACT

An optical imaging method based on a feedback principle in which the specific scan pattern is adapted according to the shape of the sample. The feedback approach produces nanometer-resolved three dimensional images of very small and moving features in live cells and in a matter of seconds. Images of microvilli in live cultured opossum kidney cells expressing NaPi co-transporter proteins with different GFP constructs and images of cell protrusions in a collagen matrix are produced with a resolution of about 20 nm. Along cell protrusions in three dimensional cellular adhesions could be identified to the extracellular matrix.

19 Claims, 7 Drawing Sheets
(5 of 7 Drawing Sheet(s) Filed in Color)

NANOMETER-SCALE OPTICAL IMAGING BY THE MODULATION TRACKING (MT) METHOD

RELATED APPLICATIONS

The present application is related to U.S. Provisional Patent Application Ser. No. 61/469,715, filed on Mar. 30, 2011, which is incorporated herein by reference and to which priority is claimed pursuant to 35 USC 119.

GOVERNMENT RIGHTS

This invention was made with Government support under Grant Nos. P41-RR003155 and P50-GM076516 awarded by the National Institutes of Health. The Government has certain rights in the invention.

BACKGROUND

1. Field of the Technology

The disclosure relates to the field of optical methods for super-resolution imaging of live cells, specifically to an optical imaging method based on a feedback principle in which the specific scan pattern is adapted according to the shape of the sample which produces nanometer-resolved three dimensional images of very small and moving features in live cells and in a matter of seconds.

2. Description of the Prior Art

Several optical microscopy techniques have been previously developed to "break" the diffraction limit and to produce nanometer-resolved images. These techniques can be broadly classified as "physical" techniques in which ingenious approaches are used to break the diffraction limit. For example the STEO (stimulated emission depletion) technique uses stimulated emission to reduce the effective size of the PSF (point spread function). Other methods have used the determination of the center of mass of the fluorescence emission due to single molecules to obtain images with nanometer resolution of cellular features. The PALM and the STORM techniques and their variants also use this approach Current methods in laser scanning confocal microscopy are based on moving a laser spot in a predetermined pattern, for example in a raster scan path, to obtain the intensity in each point of a plane of focus. These scanning techniques are inefficient however when the features to be imaged are at the nanoscale and sparse since the scanning path crosses the object to be imaged in only a few points. The efficiency of a predetermined scanning pattern, defined as the ratio of the time the laser beam is on a feature with respect to the total time of scanning, further decreases in three dimensions. Live cell structures like protrusions or microvilli are continually remodeled changing shape and position. Current imaging methods, including the super-resolution techniques known as STED and PALM, are inadequate to detect the dynamic of chemical reactions in these tiny three dimensional structures, which occur in the millisecond to second time scale.

BRIEF SUMMARY

The illustrated embodiments are directed to an optical imaging method which does not scan the sample with a predetermined pattern. Instead, the illustrated embodiments are based on a feedback principle in which the path followed by the laser spot is decided during the laser scan according to the shape of the features of the object which is being scanned. The feedback algorithm is designed to surf a laser spot with a known point spread function at a constant distance from a fluorescent surface. Since we know the position of the laser spot, its point spread function, and the distance from the surface, we can reconstruct the shape of the object. The uncertainty in the determination of the shape of the object depends on the error in the determination of the position of the laser spot, which is generally in the nanometer range. This feedback imaging approach produces high quality three dimensional images in seconds and does not require sample fixation.

When an illumination spot approaches a fluorescent surface, the total fluorescence emitted depends on the distance of the spot from the surface, but also depends on the number of fluorophores on the surface. Therefore, the fluorescence intensity alone cannot be used to determine the distance of the spot from the fluorescent surface. The center position of the spot is then rapidly oscillated closely and perpendicularly to the surface, i.e. in a direction perpendicular to the direction of the laser beam. Due to the non-linear quasi Gaussian shape of the laser spot (the point spread function, PSF), the modulation of the fluorescence caused by the oscillating spot depends on the distance of the center of the spot from the surface. The modulation of the fluorescence is the ratio between an alternating part due to the rapid oscillation of the spot and an average part due to the local fluorescence of the surface. This method, called modulation tracking (MT), does not use the diffraction of the light and therefore does not break the diffraction limit. The sensitivity of MT to the distance of the center of the laser spot from the fluorescent surface depends on the precision of the measurement of the modulation function, which depends on the total number of photons collected at each point of the scan and on the slope of the modulation tracking function. The slope depends on the spatial derivative of the PSF.

In one specific application of the MT technique, three dimensional images of moving microvilli on the surface of opossum kidney (OK) cells are shown. The study of microvilli structure and dynamics in vivo is of great importance in biology and physiology since the microvillus is a common motif found in kidneys, intestine and lungs. The microvilli are several micrometer long structures with a diameter of about 100 nm. Each cell has many microvilli that appear at the apical membrane. The co-transporter proteins NaPi-2a-Cerulean and NaPi-2c-YFP concentrate at the microvilli to give rise to diffuse fluorescence as seen in confocal images. None of the current nano-imaging optical methods are capable of measuring the clustering dynamics of proteins on the surface of rapidly moving (on the second time scale) microvilli. Instead the MT method gives high resolution images of the moving microvilli and shows transient differential clustering of the NaPi-2a and NaPi-2c proteins using ratio imaging at the microvilli surface. The diffusion of proteins molecules on the surface of microvilli using fluctuation correlation spectroscopy performed during imaging was also measured. However, it is to be expressly understood that the scope of the invention is not limited to imaging microvilli or for that matter features of cellular objects or cells, but may be employed on any kind of nanometer sized moving feature.

In another specific embodiment, the MT technique produces three dimensional images of cell protrusions in which cells form adhesion with the extracellular matrix. In this case the protrusions could be very long (20-50 um) and the diameter is variable (0.2 um to 1 um). For the images of protrusions we also show simultaneous data acquisition in two colors.

In our implementation of the MT imaging methodology, the first step is to obtain an overall image of the area of the sample which is being studied; which is done using the common raster scan operation of the laser scanning microscope. Next, then each sample is analyzed to scan a specific structure in three dimensions. For example, in the case of the imaging of a microvillus, we first obtain a confocal image of the apical membrane and then we start the local three dimensional imaging at one microvillus.

The current invention provides for a method of optical imaging for producing a nanometer-resolved three dimensional image of a feature of an object including oscillating a position of a laser spot having a cross section characterized by a point spread function with a width, the laser spot being oscillated at a scan position at a perpendicular distance from a surface of the feature within the width of the point spread function of the laser spot using feedback control of the perpendicular distance. A returned signal is then detected from the feature of the object and the perpendicular distance of the laser spot from the surface is measured in real time upon detection of the returned signal using a modulation function. The feature of the object is scanned at a plurality of selective feedback controlled scan positions. This oscillating, detecting and measuring in repeated three dimensional scans is done several times to acquire an ensemble of corresponding measured perpendicular distances. Finally, a three dimensional image of the shape of the feature of the object is constructed from the ensemble of corresponding measured perpendicular distances and scan positions of the oscillating laser spot during scanning.

In a separate embodiment, the method step of oscillating the position of a laser spot at a perpendicular distance from the surface using feedback control includes moving the laser spot around the surface of the feature in a circular orbit. The three dimensional image of the shape of the feature may also be constructed by calculating the distance from the circular orbit to the surface of the feature at a plurality of angles therefrom to produce a polygon. In this embodiment, the feature of the object has an axis and the method may also further include moving the plane of the circular orbit of the laser spot in the direction of the axis of the feature, producing a plurality of polygons at a plurality of planes along the axis of the feature, stacking the plurality of polygons to provide a three dimensional mesh representing the three dimensional structure of the feature, and then covering the mesh with a texture.

In another embodiment, the method further includes maintaining the laser spot a constant measured distance from the surface of the feature.

In yet another embodiment, the method step of where the surface is a fluorescent surface, where the returned signal is a fluorescent signal, and where producing nanometer-resolved three dimensional images of a feature all include producing nanometer-resolved three dimensional images of small and sparse features of live cells.

In a further embodiment, the method step of where the surface is a fluorescent surface, where the returned signal is a fluorescent signal, and where producing nanometer-resolved three dimensional images of a feature includes producing nanometer-resolved three dimensional images of cell protrusions in neurons, protrusions formed during cell movements or other typical cellular structures like microvilli, and the localization of specific molecules mapped on the surface of the feature.

In yet another embodiment, the method step of where the surface is a fluorescent surface, where the returned signal is a fluorescent signal, further includes performing fluorescence correlation spectroscopy (FCS) while reconstructing the shape of the feature to measure molecular diffusion within the feature.

In yet another embodiment, the method step of oscillating the position of a laser spot at a distance from the surface of the feature using feedback control further includes using feedback according to the shape of the surface of the feature.

In a separate embodiment, the method step of oscillating a known position of a laser spot at a distance from a surface of the feature using feedback control further includes using the feedback control without sample fixation.

In another embodiment, the method step of where the surface is a fluorescent surface, where the returned signal is a fluorescent signal, wherein constructing the three dimensional image of the shape of the feature includes producing three dimensional images of moving cellular structures of the feature.

In another embodiment, the method step of where the surface is a fluorescent surface, where the returned signal is a fluorescent signal, further includes performing raster-scan image correlation spectroscopy (RIGS) while constructing the three dimensional image of the shape of the feature to measure molecular diffusion within the feature.

In another embodiment, the method step of constructing the three dimensional image of the shape of the feature includes imagining protein dynamics on the mobile cellular structures of the feature.

In yet another embodiment, the method further includes producing a confocal laser spot which can be rapidly moved in three dimensions.

In another embodiment, the method step of oscillating a position of the laser spot includes controlling the movement of the laser spot along a software determined trajectory in response to a measured modulation at a given position of the feature.

Lastly, the method step of constructing the three dimensional image of the shape of the feature of the object may also include a three dimensional image of the shape of non-fluorescent structures of the feature of the object.

The current invention also provides for an apparatus to allow for the production of nanometer-resolved three dimensional images of a feature of an object. The apparatus includes a laser having a controllable laser spot having a cross section characterized by a point spread function with a width and a circuit coupled to the laser for oscillating the laser spot at a scan position at a perpendicular distance from a fluorescent surface of the feature within the width of the point spread function of the laser spot using feedback control of the perpendicular distance. A detector for receiving a returned signal from the fluorescent surface of the feature is also present, along with a software controlled circuit coupled to the detector, and a scanner circuit coupled to the laser.

In one particular embodiment, the software controlled circuit of the apparatus performs fluorescence correlation spectroscopy (FCS) to measure molecular diffusion within the feature when the scanner circuit is being operated to construct a three dimensional image of the shape of the feature.

In another embodiment, the software controlled circuit of the apparatus performs raster-scan image correlation spectroscopy (RIGS) to measure molecular diffusion within the feature when the scanner circuit is being operated to reconstruct a three dimensional image of the shape of the feature.

In yet another embodiment, the laser of the apparatus is a confocal laser.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The disclosure can be better visualized by turning now to the following drawings wherein like elements are referenced by like numerals.

BRIEF DESCRIPTION OF THE DRAWINGS

The specification contains at least one drawing executed in color. Copies of this patent or patent application publication with color drawing(s) will be provided by the Office upon request and payment of the necessary fee.

The disclosure and its various embodiments can now be better understood by turning to the following detailed description of the preferred embodiments which are presented as illustrated examples of the embodiments defined in the claims. It is expressly understood that the embodiments as defined by the claims may be broader than the illustrated embodiments described below.

DETAILED DESCRIPTION OF THE PREFERRED EMBODIMENTS

The illustrated embodiments include an optical imaging method for producing nanometer-resolved three dimensional images of very small and moving features in live cells and in a matter of seconds. The method keeps the laser spot at a constant distance from a fluorescent surface using feedback control. The distance from the surface is determined in real time during the acquisition. Since the position of the laser spot and the distance from the surface is known, the shape of the object can be reconstructed.

One of the objects of the illustrated embodiments is to image small and sparse features of live cells. These features can be cell protrusions, typical of cell types like neurons, protrusion forming during cell movements or other typical cellular structures like microvilli. The shape of these features are reconstructed with nanometer resolution and the localization of specific molecules mapped on their surface. This approach to nano-imaging allows us to perform fluorescence correlation spectroscopy (FCS), while imaging to measure molecular diffusion within the cellular structures.

Instead of moving the laser spot in a predetermined pattern, we use a feedback principle in which the scanning pattern is decided during the scan according to the shape of features present in the sample.

Because the optical imaging method does not scan the sample with a predetermined pattern and is based on a feedback principle in which the path followed by the laser spot is decided during the scan according to the shape of objects present in the sample, it is very efficient for the imaging of small cellular structures. This feedback imaging approach produces high quality three dimensional images in seconds and does not require sample fixation. The method produces three dimensional images of moving cellular structures. It works with live cells and is compatible with correlation techniques like FCS and RICS. The method is able to follow protein dynamics on mobile cellular structures where important biochemical reactions may occur.

Thus, the method is usable in biology, biophotonics, and biomedical research for fast high quality three dimensional imaging. This method can be implemented in microscopes that produce a small illumination spot such as confocal and two-photon excitation microscopes and where the spot can be rapidly moved in three dimensions. The implementation of the method only requires the appropriate software to move the scanner along specific trajectories in response to a measured modulation at a given position. The illustrated embodiments can be used for the imaging of many kinds of cellular structures which are important for specific cell functions. Examples include protrusions typical of cell types like neurons, protrusions forming during cell movement, and epithelial cell microvilli. The imaging of cell protrusions can be performed on live cells to study molecular interactions and dynamics governing such processes as synapse formation or cell migration. Imaging of microvilli on kidney or intestine cells is relevant for understanding the basic molecular interactions regulating absorption of nutrients. The method can also be used in tissues, if coupled to a microscope which is capable of imaging in depth. In principle the method can also be used to image nonfluorescent structures, using any optical signal detectable with a scanning microscope, for instance second harmonic generation (SHG) or reflection.

There are two aspects of the modulation tracking technique that allow us 1) to track the average position of the structure we are imaging and 2) to determine the three dimensional shape of the object. The feedback orbital technique that allows tracking of rapidly moving fluorescent particles in three dimensions is well known. For a point particle, we showed that the center of mass can be measured with an error that depends on the width of the PSF and the total intensity that can be collected along an orbit. This error is on the order of nanometers for reasonably bright structures. In the case of a microvillus, we have many fluorescent molecules on the membrane and the intensity is about $10^5$ to $10^6$ counts/s which results in nanometer precision of the center of mass of the microvilli. In the MT technique the orbital motion is used to track the position of the center of mass of a fluorescence distribution, namely the microvillus center at a given height.

Figure 1:
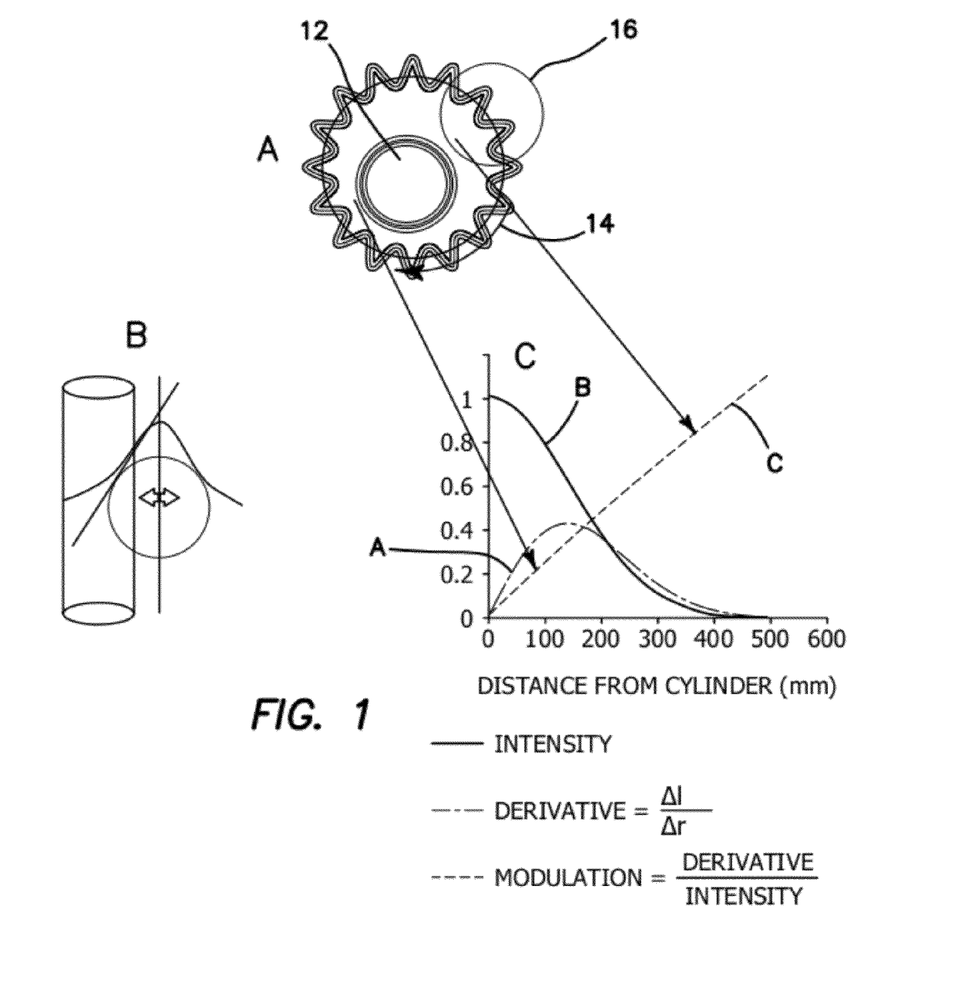
FIG. 1A is a schematic diagram of the modulation tracking technique of the current invention, specifically how the laser is moved about a circular orbit about the feature to be imaged.
FIG. 1B is a schematic diagram of how the radius of the orbit is modulated at high frequency.
FIG. 1C is a schematic diagram of how the small oscillation of the radius effectively computes the spatial derivative.
Figure 2:
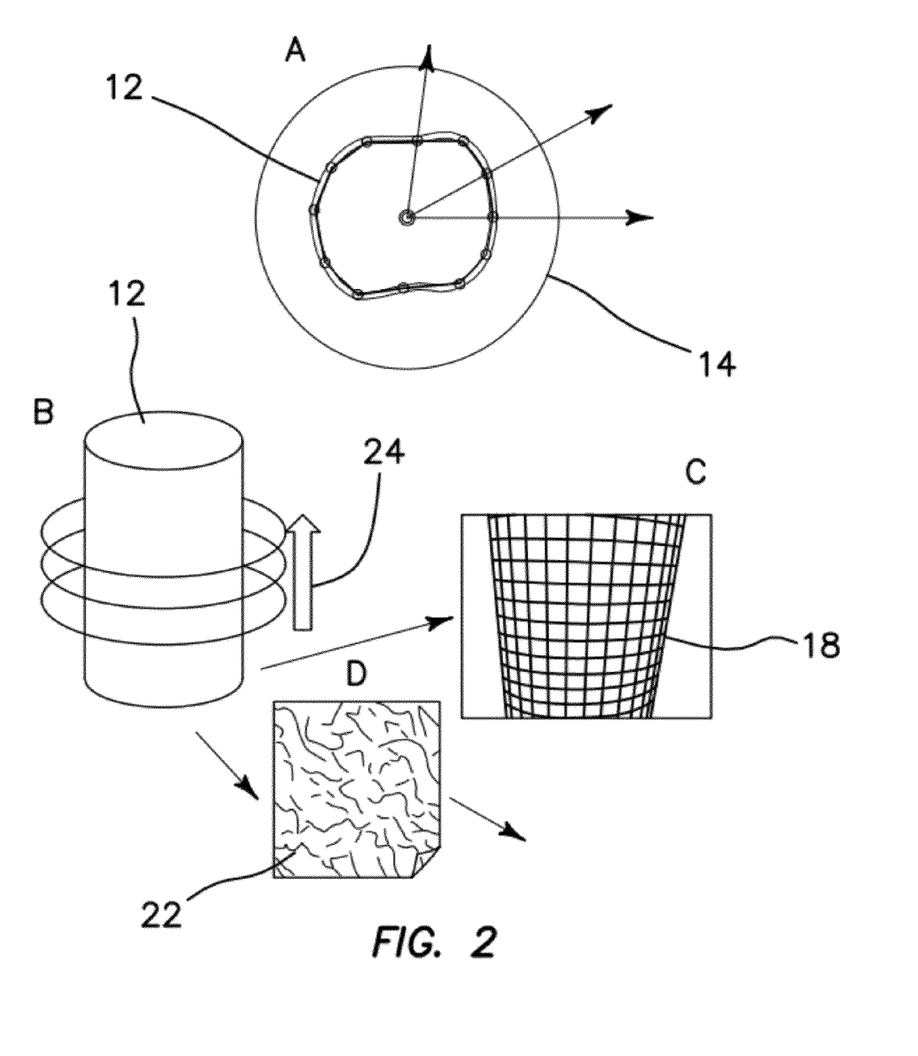
FIG. 2A is a schematic diagram of how as the laser goes around the feature, the local modulation function gives the distance of the surface from the average orbit.
FIG. 2B is a schematic diagram of how the orbital plane is moved along the cylinder axis of the feature.
FIG. 2C is a schematic diagram of a polygon produced by an orbital plane shown in FIG. 2B.
FIG. 2D is a schematic diagram a mesh created by a plurality of stacked polygons shown in FIG. 2C.

FIGS. 1A and 2A are schematics which illustrate the current modulation tracking technique. To obtain the shape of the feature 12 at one particular orbital plane, we rapidly oscillate the radius of the orbit 14 and then we determine the distance of the object surface 12 from the orbit 14 using the modulation function. The laser spot 16 preferably oscillates along the orbit 14 path according to a trajectory as determined by programmable software as is known in the art. FIGS. 1A-1C shows the principle of the measurement and the physical origin of the modulation function. The modulation changes approximately linearly up to about 500 nm from the surface of the feature 12. At larger distances the intensity becomes too small for the modulation to be useful. This range depends on the size of the PSF. The modulation can be measured with 1% error at the light levels of our experiments, which results in about 10 nm error for the determination of the distance of the fluorescent surface.

FIG. 1A shows that the scanner is programmed to move the laser beam spot 16 around a microvillus or other feature 12 to be imaged in a circular orbit 14, the orbit 14 comprising a radius larger than the average radius of the feature 12 which is modeled as a cylinder in the figure. It should pointed out however that the feature 12 is modeled as a cylinder for illustrative purposes only. Other models approximating other shapes known to those skilled in the art may be used without departing from the original spirit and scope of the invention. The radius of the orbit 14 is modulated at high frequency as shown in FIG. 1B. When the illumination spot 16 approaches the surface of the microvillus 12, due to the modulation of the orbit radius 14, the fluorescence intensity increases as schematically shown in FIG. 1B. The small oscillation of the radius effectively computes the spatial derivative as shown in FIG. 1C. Curve A represents the intensity profile of the spot 16 (the PSF). Curve B represents the spatial derivative of the intensity profile. Curve C is the ratio of Curve A to Curve B. This ratio is the modulation function which depends on the distance from the surface of the feature 12. The modulation function increases quasi-linearly as a function of the distance from the surface of the feature 12. By providing a feedback to the average orbit radius 14 we can maintain the modulation constant, for example at a value of 0.5. The modulation function gives the distance of the surface of the feature 12 according to Curve C for every value of the modulation.

FIGS. 2A-2C are schematics of the method to determine the three dimensional shape of the feature or object 12. FIG. 2A illustrates that as we go around the feature 12, the local modulation function gives the distance of the surface from the average orbit 14. In FIG. 2A, the modulation value is converted in distance from the orbit 14 according to the modulation function that was calculated using simulated uniform cylindrical distribution of fluorescence and further verified using empty capsule fluorescent beads. This distance is calculated at several angles giving a polygon which is used to approximate the shape of the surface of the feature 12 at the orbital plane 20. This polygon is then interpolated to 128 points to produce a smooth line as shown in FIG. 2B. The orbital plane 20 is then moved along the cylinder axis. For each plane 20 we produce a polygon 18 as shown in FIG. 2C. A plurality of polygons 18 are then stacked to provide a mesh 22 which represents the three dimensional structure of the object 12 we are imaging as shown in FIG. 2D. The three dimensional mesh 22 is covered by a texture given by a specific quantity like the fluorescence intensity or the intensity ratio of two channels.

This procedure produces a polygonal shape 18, mapping the fluorescent surface at a given orbital plane 20. The number of points of the polygon 18 depends on the number of oscillations of the radius during one orbit. We use a number of oscillations between 8 and 32, depending on the size of the object 12. The polygon 18 is interpolated to 128 points to produce a smooth line. We then move the orbit plane 20 in the direction of the axis of the feature 12 we are examining, which is the vertical axis represented by arrow 24 in the case of microvilli seen in FIG. 2B. A new polygon 18 is obtained and the process continues until we reach the end of the feature 12, indicated by a sudden drop of the fluorescence intensity below a given threshold. The stack of polygons 18 obtained form 3-dimensional mesh 22 that directly corresponds to the shape of the object seen in FIG. 2C.

Once the three dimensional mesh 22 has been determined with nanometer resolution we add a texture to the mesh 22 according to selected functions such as the fluorescence intensity or fluorescence ratio as seen in FIG. 2D. We note that although the shape of the feature 12 can be determined with nanometer precision, the resolution of molecules (or cluster of molecules) on the feature 12 surface is limited by diffraction. In principle we could use the super-resolution techniques mentioned in the introduction to increase the resolution of the distribution of the fluorescence at the feature 12 surface or use deconvolution techniques, in order to determine the distribution of different molecular species on the surface.

The resolution of the shape of the feature 12 along the z-axis (the long axis of a microvillus, for example) depends in part on the size of the illumination spot 16. We performed simulations of cylinders with a step change in diameter from 100 nm to 180 nm radius. In every case we were able to recover the cylinder diameter within 10 nm, but the transition between the two radii was occurring during a length approximately equal to the axial waist of the PSF. If the feature 12 is horizontal, the resolution of the step depends on the radial waist of the PSF, which is generally a factor of 3 smaller than in the axial direction.

The current MT method does not require fixed samples. One segment of the feature 12 can be measured in about 16 ms in our system. Even for a fast moving microvilli (i.e., in the second range) can be imaged. The three dimensional image is obtained directly from the mesh 22 given by moving the position of the orbit 20 along the axis of the feature 12 (that is, up and down the microvillus). The scanning of a cylindrical surface is equivalent to the raster scan of a flat surface without retracing. Therefore we apply the principles of raster-scan image correlation spectroscopy (RIGS) to obtain the diffusion and concentration of fluorescent molecules on the microvillus surface making MT a truly dynamic nanoimaging technique. The MT technique has the capability to identify specific molecules on the surface of the feature 12, including their clustering and dynamics in a millisecond time scale.

There are other optical techniques capable of measuring the height of structures based on interferometric measurements and optical profilometry. These techniques have very high resolution in the direction parallel to the light propagation while the resolution in the x-y plane is limited by diffraction. Interferometric techniques don't allow the reconstruction of three dimensional objects like microvilli or cell protrusion at the nanometer scale. Also, interferometry is based on reflectivity and suffers from lack of selectivity attained by fluorescence.

Figure 3A:
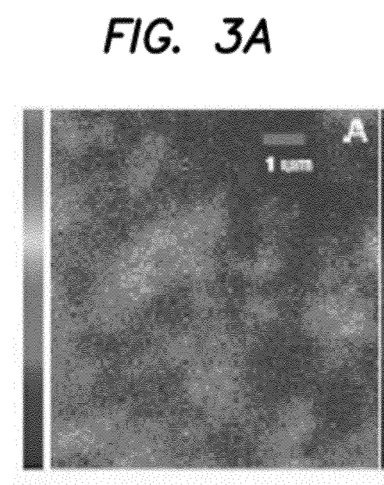
FIG. 3A is a color image showing an x-y plane image of an OK cell expressing NaPi-2a-Cerulean obtained by the current invention.
Figure 3B:
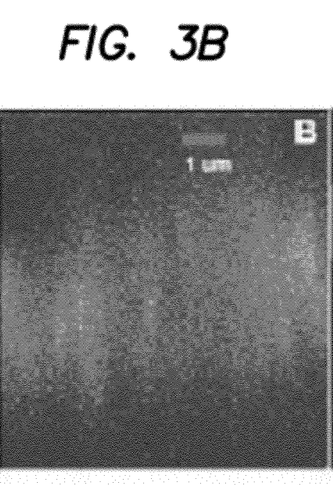
FIG. 3B is a color image showing an x-z plane image the cell seen in FIG. 3A obtained by the current invention.
Figure 3C:
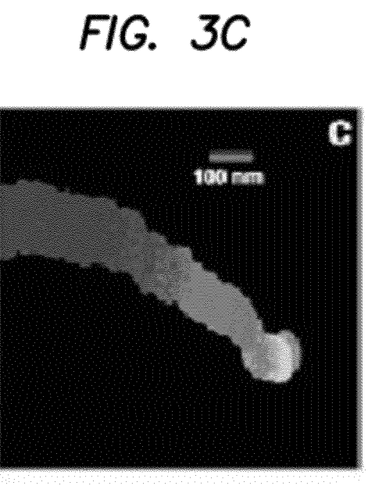
FIG. 3C is a color image showing a reconstructed three dimensional image of one microvillus using the current invention.

The following description relates to the nanoimaging of a microvillus, however it should expressly understood that other objects or biomedical samples may also be the subject of the present method without departing from the original spirit and scope of the invention. FIG. 3A-3C shows images obtained using the Zeiss LSM510 microscope taken in the x-y plane and x-z plane of OK cells transfected with NaPi-2a-Cerulean and the three dimensional reconstruction using the current MT technique. The microvilli can be barely identified in the confocal images since they are too small to be resolved and also because they are moving. The x-z image shows the microvilli extending for about 5 um as seen in FIG. 3A. FIG. 3A also shows an x-y plane image of OK cell expressing NaPi-2a-Cerulean. The microvilli appear as the roundish bright areas in this projection. For the three dimensional MT imaging the scanner was centered at one microvillus, in a region with few sparse microvilli. Then the tracking routine was started. The z-position of the orbit 14 was moved for a height of about 2 um in 10 s starting at the base of the villus. Detail of the same cell imaged in the x-z plane showing adjacent microvilli may be seen in FIG. 3B. The color scale in FIGS. 3A and 3B corresponds to 0 to 256 levels of the analog output of the LSM 510 microscope.

FIG. 3C shows the reconstructed three dimensional image of one microvillus using the current MT technique. The surface of the recovered image is painted according to the fluorescence intensity. The surface was reconstructed at a resolution of 2 nm for the center of the microvillus and about 20 nm for the radius. This nanometer three dimensional reconstruction of the microvillus shows a convoluted tortuous structure. The average diameter of the microvillus is about 100 nm. The protein concentration, as judged from the fluorescence intensity, changes along the microvillus. The region reconstructed is about 2 um long. The color scale of FIG. 3C corresponds to 0-256 KHz of the photon counting acquisition electronics of the M5 microscope. The brightest part is toward the base of the microvillus. Note the non-uniform distribution of the fluorescence along the microvillus.

Figure 4:
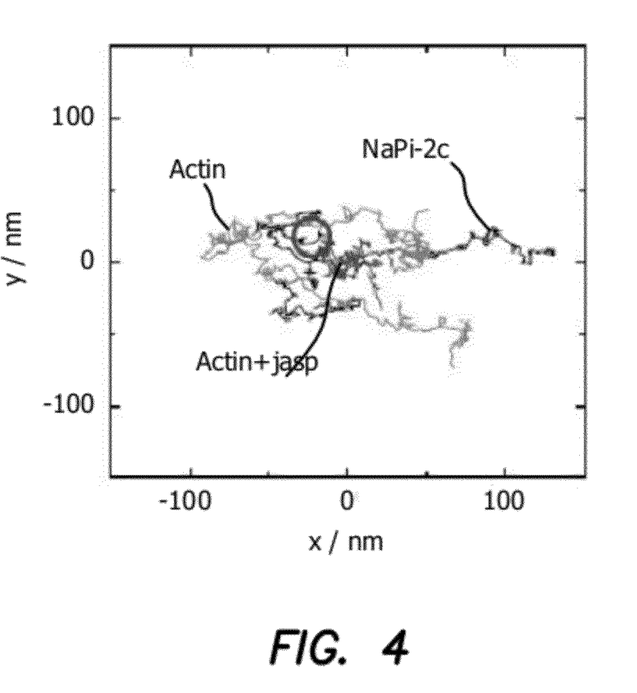
FIG. 4 is a color plot of the dynamics of the center of mass of one microvillus imaged by the current invention.

Not all microvilli have the same tortuosity. Some of the microvilli appear straighter. When we scanned the same microvillus back and forth, we found that the microvillus moved during the scan. The time scale of movement also changed among the microvilli. All the microvilli moved during a 20 s scan. Some of the microvilli show regions of higher fluorescence intensity along the surface, indicating that clustering of the protein was occurring. The typical dynamics of the center of mass of one microvillus is shown in FIG. 4. In this experiment the z-coordinate was kept constant and the feedback mechanism kept the orbit 14 centered on the microvillus at a given height. The microvillus moves about 100 nm in the y direction and 200 nm in the x direction over the course of this experiment. The trace of the microvillus center of mass is painted with colors that change every 5 s, demonstrating the relatively fast motion of the microvillus and the recovery of the center of mass of the microvillus position with nanometer resolution.

Figure 5:
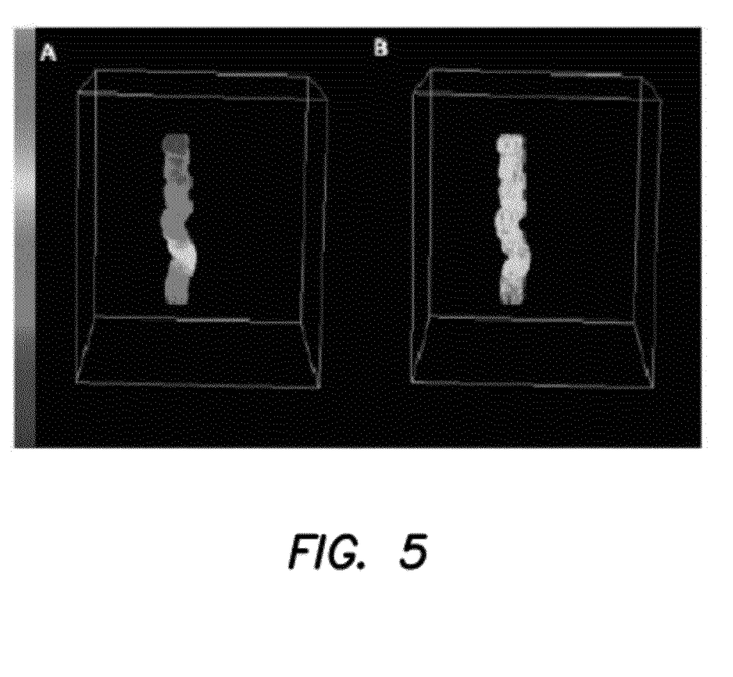
FIG. 5 is a color distribution of fluorescence distribution of NaPi-2a-Cerulean along a microvillus in the left panel, and a color distribution of the same microvillus painted according to the normalized ratio function of the intensities in the two channels in the right panel.

The MT method allows imaging of the protein distribution on the microvillar membrane. We imaged microvilli in OK cells co-transfected with NaPi-2a-Cerulean and NaPi-2c-YFP. For the example shown in FIGS. 6A and 6B, the length of the orbit 14 is 1.256 um. We can clearly distinguish that the fluorescence distribution of NaPi-2a-Cerulean is not uniform along this microvillus as seen in the left panel of FIG. 5. Along the microvillus, the fluorescence is distributed along bands that seem to concentrate in only one side of the microvillus at the microvillus base. The size of the protein patches shown in FIG. 5 is determined by the PSF. Therefore the actual size of these domains could be smaller.

The right panel of FIG. 5 shows the image of the same microvillus painted according to the normalized ratio function of the intensities in the two channels or GP. The GP image is relatively uniform along the circumference of the microvillus but has bands along the microvillus length showing that the two proteins are not equally distributed along the microvillus. The width of the structures along the microvillus is on the order of 250 nm, again consistent with the size of the illumination spot 16. These structures are dynamic, as they can disappear or appear at a different location when we image a microvillus at subsequent times, for example at $\Delta t=20$ s.

Figure 6A:
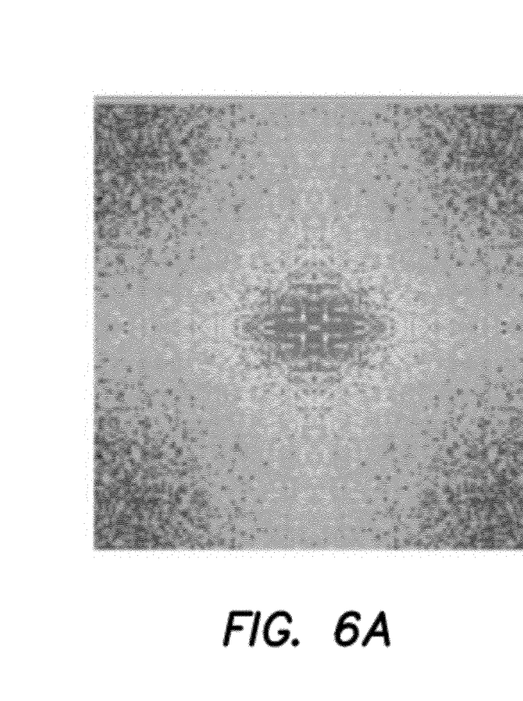
FIG. 6A is a color image of the result of the dynamic RIGS (Raster-scan Image Correlation Spectroscopy) analysis performed by the current invention to observe the motion of molecules on a microvilli membrane surface.
Figure 6B:
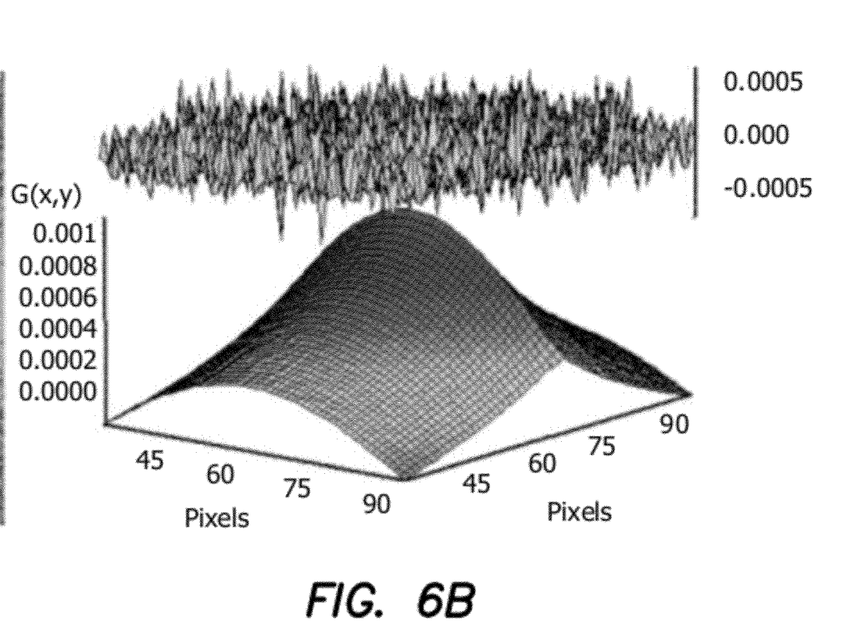
FIG. 6B is a 3D color image of the 2D results seen in FIG. 6A.

We are performing a circular scanning of the feature 12 at relatively high speed. Every pixel is measured for about 62.5 microseconds and pixels along the orbit 14 are separated by 0.01 um. We performed a dynamic RIGS (Raster-scan Image Correlation Spectroscopy) analysis as seen in FIG. 6A to observe the motion of molecules on the microvilli membrane surface. We found that Cerulean-NaPi2c has a local diffusion coefficient of about 0.02 $um^2$/s using a model for 2D diffusion as seen in FIG. 6B.

Figure 7A:
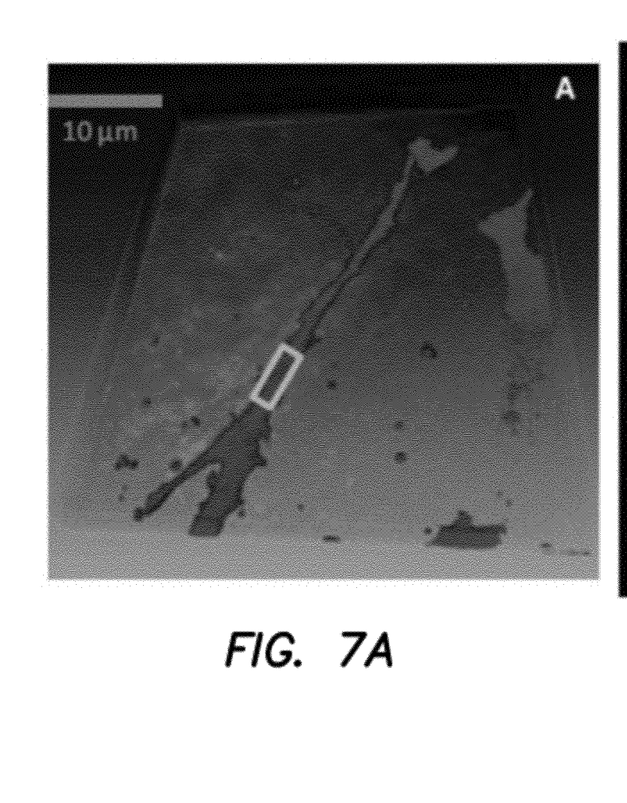
FIG. 7A is a color image of a protrusion of a MB231 cell expressing Paxillin-EGFP growing in a three dimensional collagen matrix obtained by the current invention.
Figure 7B:
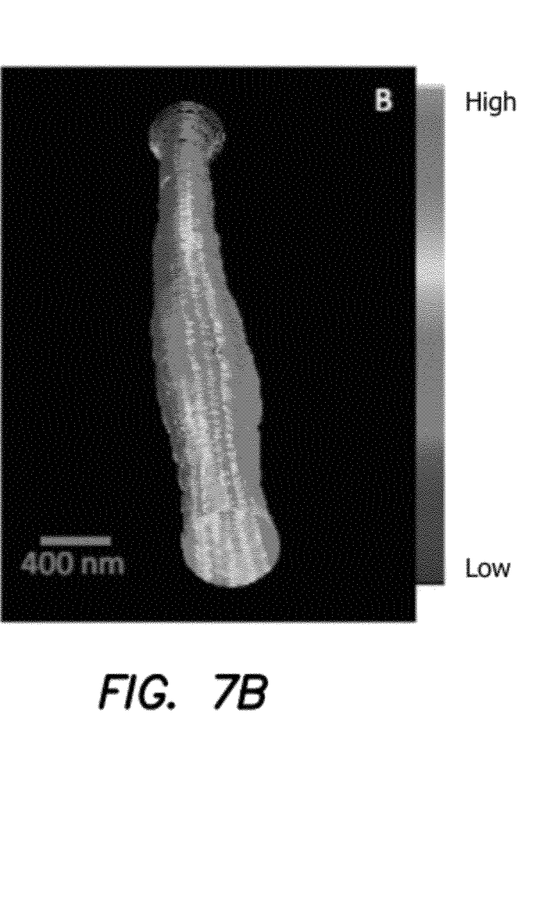
FIG. 7B is a magnified color image of the protrusion seen in FIG. 7A at the nanometer scale.

FIG. 7A shows the image of a protrusion of a MB231 cell expressing Paxillin-EGFP growing in a three dimensional collagen matrix. We first image a large field using the raster scan path and then we "dive in" to image the three dimensional protrusion at the nanoscale as seen in FIG. 7B. The protrusion has a larger diameter than a microvillus and also the diameter changes along the protrusion. The fluorescence intensity is larger at some specific regions along the cell body, presumably where the cell contacts the collagen.

In the current MT technique the position of a fluorescent surface is determined by the modulation of the fluorescence signal as a function of the distance from the surface. Since the intensity as a function of the distance from the surface changes non-linearly, using the modulation of the light we effectively measure the derivative of the fluorescence intensity as a function of the distance from the surface with relatively high precision. We then produce a topographical map of the fluorescent surface using the modulation function. In the case of microvilli imaging, we measure the deviation of the center of mass and the deviations of the radius with nanometer accuracy. This is possible because we transformed the measurement of the shape of the microvilli in the measurement of the topography of its surface. Instead, in the direction along the microvillus surface the topographical resolution cannot be any better than the size of the spot 16 used. However, established methods as these based on deconvolution or super-resolution can be used to locate fluorophores on the surface of the membrane with higher resolution. Since the current MT technique is based on the measurement of the modulation function (ratio of the alternate to the constant part), bleaching of the fluorescence at the surface has a minimal effect on the determination of the three dimensional shape.

The current MT technique may also be applied to quasi cylindrical structures. For this symmetrical shape, the MT feedback method is particularly efficient. However, the method could be applied to arbitrarily shaped surfaces since the feedback based on the modulation function moves the illumination spot 16 at a constant distance from the surface. There is a limit in the speed of scanning of the surface, which depends on the galvo scanner used in our instrument for the modulation in the xy plane and of the piezo that we use to move the laser spot 16 along the z-axis. In our instrument the maximum scanning frequency we can achieve is about 2 kHz in the x-y direction and 200 Hz in the z direction, respectively. Another consideration is that the shape of the PSF is different in the radial and in the axial direction of the microscope. Since the shape of the PSF only determines the slope of the PSF and this slope is measured independently, the shape of the PSF is taken into account in the feedback algorithm and therefore the shape of the object is determined accurately in the three directions. However, as noted before, the error in the determination of the surface position is larger in the radial direction. Interestingly, the resolution of steps in shape changes is better when the cylindrical object is laying horizontally since the PSF is narrow in the radial direction.

The current MT imaging approach can also be applied to live cells. The motion of the microvilli is tracked and the assignment of the fluorescence intensity to a voxel in space and time is accurate with respect to the microvillus surface. Scanning along the surface provides direct visualization of how proteins are distributed on a three dimensional membrane structure like the microvillus, a feature that can be important for the study of the NaPi transporters regulation and more in general for studying membrane micro domain organization. More importantly, the circular scanning along the membrane surface allows fluorescence image correlation techniques to be applied. Since the microvillus is always at the center of the orbit 20, if we keep the z-axis constant, we can measure the fluorescence along the orbit and the fluorescence fluctuations due to the diffusion of molecules. This is equivalent of the RIGS scanning experiment. It provides information about the diffusion and the brightness of the fluorescent molecules in the membrane. This is a unique possibility offered by the MT approach.

The current MT method can be implemented in microscopes that produce a small illumination spot 16 such as confocal and 2-photon excitation microscopes and where the spot 16 can be rapidly moved in three dimensions. The implementation of the method only requires the appropriate software to move the scanner along specific trajectories in response to a measured modulation at a given position. The three dimensional structure of the surface of a microvillus 12 is obtained with much higher resolution than techniques based on the localization of fluorescent molecules. The method works in the presence of many molecules and it does not require a particular hardware or high illumination power.

The strength of the current MT technique is its capability to follow molecular events such as diffusion and interactions directly in three dimensions at a time and spatial scale that cannot be obtained with current optical techniques. There is growing interest in live cell imaging to display cellular processes at the millisecond to second time scale. The current MT imaging technique is exquisitely dynamic and therefore ideal for the study of such processes. Since MT is essentially a tracking technique, it is very efficient for imaging objects that are spatially isolated, while it is difficult to use in a crowded field.

A specific example for carrying out the current MT method is given below. Opossum kidney (OK) cell culture was performed as discussed above. Briefly, cells were grown in Dulbecco's modified Eagle's medium (DMEM/F12) supplemented with 10% fetal bovine serum, penicillin, streptomycin and L-glutamine in a humidified 5% $CO_2$-95% air atmosphere incubator at 37° C. Transfections and cotransfections were achieved with Lipofectamine 2000 (Invitrogen) and cells at 90% confluency, following the manufacturer's instructions. OK cells expressing the fluorescent fusion proteins were grown on poly-L-lysine-coated eight-well Lab-Tek chambered coverglass (Nunc). Measurements were performed 24-48 hours after transfection. Type I rat tail collagen was prepared with 10×PBS and $H_2O$ at 2.5 mg/ml final concentration and adjusted to pH=7.4 using 10N NaOH. MDA MB231 stable cells lines expressing paxillin-EGFP at a concentration of $0.25 \times 10^6$ were mixed with the collagen and allowed to polymerize for 1 hour at 25° C. without FBS supplemented media. Then they were incubated at 37° C. overnight before imaging.

A Zeiss 510 LSM microscope (Jena, Germany), equipped with a Confocor 3 unit and the META detector was used for the x-y and x-z images. The argon ion laser with excitation at 456 nm (2% power) and 514 nm (0.5% power) was used to excite the cerulean and the YFP constructs, respectively. Images were obtained in the 256×256 format with a pixel dwell time of 12.5 us and a zoom of 12. Data were saved in the lsm format and further processed by the SimFCS software (www.lfd.uci.edu, UCI, Irvine). For the x-z images the "fast z" acquisition mode of the LSM 510 was used. The modulation tracking system was implemented in the M5 microscope at the LFD previously described. Briefly, this microscope is built around an Olympus X71 body. The light source is a Chameleon Ultra II laser (Coherent, CA) that produces 2-photon excitation of the cerulean and the YFP constructs. The laser power was set between 20 and 30 mW, measured before entering the microscope. The laser wavelength was set at 820 and 940 nm for cerulean and YFP excitation, respectively. Two GaAS detector H7241P (Hamamatsu, Japan) were used to acquire the fluorescence in the 380-480 nm range and 500-550 nm for the two channels, respectively. The galvano scanner (Cambridge Technology, MA) was driven by the ISS-3axis card (ISS, Champaign Ill.) as well as the piezo z-axis (Phisik Instrument, Germany). The circular orbital pattern and the modulation pattern was stored in the memory of the ISS-3axis card and the center offset in the x-y position was updated according to the tracking mechanism every 16 ms. The fluorescence intensity at 128 points along the orbit 20 was collected at a sampling rate of 8 kHZ. The modulation of the orbit 20 was set at a period of 2 ms. We determined that the 3 dB point of the scanner response in the x-y plane was 3 ms. We used an amplitude modulation for the modulation tracking that gives 10% modulation of the orbit radius. The orbit radius was initially set at different values between 200 nm and 400 nm, depending on the diameter of the microvillus 12. The feedback mechanism changed the radius until a constant modulation of 10% was obtained along the orbit 20. Under this condition the laser spot 16 is travelling at a constant distance from the fluorescent surface. Then the plane of the orbit 20 is moved along the surface 12 cylindrical axis. The local direction of the surface axis is obtained by comparing the center of the orbit 20 at two different positions along the axis. If the object 12 starts to bend, then the direction of the subsequent orbit 20 is changed so that the orbit 20 is always perpendicular to the axis of the object and centered on the axis. The PSF of our instrument at any given experimental condition (wavelength of excitation, laser power, etc) was measured prior to each tracking measurement using 20 nm beads fixed on a slide. The size of the PSF only influences the amount of modulation of the MT technique but it does not affect the size of the objects that were imaged. The calibration of the modulation tracking function was performed using fluorescent beads shells of known diameter (15 um diameter, Invitrogen Carlsbad Calif.). Most of the measurements were done using an air objective (Olympus, 0.9NA x60 W). The position of the orbit plane along the object axis was moved with a ramp function that is variable in amplitude and period. The amplitude was set between 1 um to 3 um and the period between 1 s and 20 s, depending on the experiments. The initial position of the circular orbit 20 was set by first acquiring an x-y image at a given z position and then pointing with the mouse to one feature that we recognized to be a microvillus 12. Then the tracking of the center of the microvillus 12 and the ramping along the microvillus 12 height are done. In live samples, the center of mass of the microvillus 12 moves during the time needed to acquire the three dimensional image. Repeating the scan up-down of the same microvillus 12 many times provided a movie of the three dimensional position of the villus 12. The intensity along the cylindrical surface is modulated according to the number of oscillations of the radius used during one orbit (generally 8). This modulation of the intensity is easily removed using a notch filter of the appropriate frequency.

Many alterations and modifications may be made by those having ordinary skill in the art without departing from the spirit and scope of the embodiments. Therefore, it must be understood that the illustrated embodiment has been set forth only for the purposes of example and that it should not be taken as limiting the embodiments as defined by the following embodiments and its various embodiments.

Therefore, it must be understood that the illustrated embodiment has been set forth only for the purposes of example and that it should not be taken as limiting the embodiments as defined by the following claims. For example, notwithstanding the fact that the elements of a claim are set forth below in a certain combination, it must be expressly understood that the embodiments includes other combinations of fewer, more or different elements, which are disclosed in above even when not initially claimed in such combinations. A teaching that two elements are combined in a claimed combination is further to be understood as also allowing for a claimed combination in which the two elements are not combined with each other, but may be used alone or combined in other combinations. The excision of any disclosed element of the embodiments is explicitly contemplated as within the scope of the embodiments.

The words used in this specification to describe the various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the embodiments.

We claim:

1. A method of optical imaging for producing a nanometer-resolved three dimensional image of a feature of an object comprising:
    moving a laser spot around a surface of the feature in a circular orbit;
    oscillating a radial position of the laser spot perpendicularly with respect to the surface of the feature as the laser spot is being moved in the circular orbit around the surface of the feature, wherein the laser spot has a cross section characterized by a point spread function with a width, the radial position of the laser spot within the circular orbit further being oscillated within the width of the point spread function of the laser spot using feedback control of the perpendicular distance;
    detecting a returned fluorescence signal from the feature of the object;
    measuring the perpendicular distance of the laser spot from the surface in real time upon detection of the returned fluorescence signal using a modulation function;
    scanning the feature of the object at a plurality of selective feedback controlled scan positions and repeating oscillating, detecting and measuring in repeated three dimensional scans to acquire an ensemble of corresponding measured perpendicular distances; and
    constructing a three dimensional image of the shape of the feature of the object from the ensemble of corresponding measured perpendicular distances and scan positions of the oscillating laser spot during scanning.

2. The method of claim 1 further comprising maintaining the laser spot a constant measured distance from the surface of the feature.

3. The method of claim 1 where constructing the three dimensional image of the shape of the feature comprises calculating the distance from the circular orbit to the surface of the feature at a plurality of angles therefrom to produce a polygon.

4. The method of claim 3 wherein the feature of the object has an axis and further comprising:
    moving the plane of the circular orbit of the laser spot in the direction of the axis of the feature;
    producing a plurality of polygons at a plurality of planes along the axis of the feature;
    stacking the plurality of polygons to provide a three dimensional mesh representing the three dimensional structure of the feature; and
    covering the mesh with a texture.

5. The method of claim 1 where the surface is a fluorescent surface and where producing nanometer-resolved three dimensional images of a feature comprises producing nanometer-resolved three dimensional images of small and sparse features of live cells.

6. The method of claim 1 where the surface is a fluorescent surface, and where producing nanometer-resolved three dimensional images of a feature comprises producing nanometer-resolved three dimensional images of cell protrusions in neurons, protrusions formed during cell movements or other typical cellular structures like microvilli, and the localization of specific molecules mapped on the surface of the feature.

7. The method of claim 1 where the surface is a fluorescent surface, and further comprising performing fluorescence correlation spectroscopy (FCS) while reconstructing the shape of the feature to measure molecular diffusion within the feature.

8. The method of claim 1 where oscillating the position of a laser spot at a distance from the surface of the feature using feedback control further comprises using feedback according to the shape of the surface of the feature.

9. The method of claim 1 wherein oscillating a known position of a laser spot at a distance from a surface of the feature using feedback control further comprises using the feedback control without sample fixation.

10. The method of claim 1 where the surface is a fluorescent surface, wherein constructing the three dimensional image of the shape of the feature comprises producing three dimensional images of moving cellular structures of the feature.

11. The method of claim 1 where the surface is a fluorescent surface, and further comprising performing raster-scan image correlation spectroscopy (RICS) while constructing the three dimensional image of the shape of the feature to measure molecular diffusion within the feature.

12. The method of claim 1 wherein constructing the three dimensional image of the shape of the feature comprises imagining protein dynamics on the mobile cellular structures of the feature.

13. The method of claim 1 further comprising producing a confocal laser spot which can be rapidly moved in three dimensions.

14. The method of claim 1 wherein oscillating a position of the laser spot comprises controlling the movement of the laser spot along a software determined trajectory in response to a measured modulation at a given position of the feature.

15. The method of claim 1 wherein constructing the three dimensional image of the shape of the feature of the object comprises a three dimensional image of the shape of non-fluorescent structures of the feature of the object.

16. An apparatus to allow for the production of nanometer-resolved three dimensional images of a feature of an object comprising:
 a laser having a controllable laser spot having a cross section characterized by a point spread function with a width;
 a circuit coupled to the laser for moving the laser spot around a fluorescent surface of the feature in a circular orbit while oscillating a radius of the circular orbit of the laser spot perpendicularly with respect to the surface of the feature as the laser spot is being moved in the circular orbit, the radius of the circular orbit of the laser spot further being oscillated within the width of the point spread function of the laser spot using feedback control of the perpendicular distance;
 a detector for receiving a returned fluorescence signal from the fluorescent surface of the feature;
 a software controlled circuit coupled to the detector; and
 a scanner circuit coupled to the laser.

17. The apparatus of claim 16 wherein the software controlled circuit performs fluorescence correlation spectroscopy (FCS) to measure molecular diffusion within the feature when the scanner circuit is being operated to construct a three dimensional image of the shape of the feature.

18. The apparatus of claim 16 wherein the software controlled circuit performs raster-scan image correlation spectroscopy (RICS) to measure molecular diffusion within the feature when the scanner circuit is being operated to reconstruct a three dimensional image of the shape of the feature.

19. The apparatus of claim 16 where the laser is a confocal laser.

* * * * *